United States Patent [19]
Sloma et al.

[11] Patent Number: 5,171,673
[45] Date of Patent: Dec. 15, 1992

[54] **EXPRESSION OF HETEROLOGOUS DNA USING THE *BACILLUS COAGULANS* AMYLASE GENE**

[75] Inventors: Alan Sloma, Watertown; Nancy M. Hannett, Medford; M. A. Stephens, Concord; Cathy F. Rudolph, Stoughton; Gerald A. Rufo, Jr., Burlington; Janice Pero, Lexington, all of Mass.

[73] Assignee: Biotechnica International, Inc., Cambridge, Mass.

[21] Appl. No.: 219,599

[22] Filed: Jul. 18, 1988

[51] Int. Cl.$^5$ .......................... C12N 9/28; C12N 1/21; C12N 15/75; C12N 21/00

[52] U.S. Cl. .................... 435/69.1; 435/202; 435/252.3; 435/252.31; 435/320.1; 435/172.3; 536/27; 935/29; 935/27

[58] Field of Search ................... 435/252.3, 221, 320.1, 435/252.31, 69.1, 172.3; 935/29, 74; 536/27

[56] References Cited

U.S. PATENT DOCUMENTS

| | | | |
|---|---|---|---|
| 4,663,280 | 5/1987 | Sloma et al. | 435/68.1 |
| 4,663,294 | 5/1987 | Yamane et al. | 435/317.1 |
| 4,690,898 | 9/1987 | Yamane et al. | 435/320.1 |
| 4,711,844 | 12/1987 | Chang et al. | 435/317.1 |

FOREIGN PATENT DOCUMENTS

0063953 3/1982 European Pat. Off. .
0207044 12/1986 European Pat. Off. .

OTHER PUBLICATIONS

Hardy et al., "Production in *B. subtilis* of hepatitus B core antigen and of major antigen of foot and mouth disease virus," (1981) *Nature* 293:481.
Piggott, et al BBRC 122:175–183, 1984.
Willemot, et al *J. Gen. Microbiol* 129:311–319, 1983.
Wang, et al *Gene* 69:39–47, 1988.
Williams et al., "Expressions of *Escherichia coli trp* genes and the mouse dihydrofolate reductase gene cloned in *Bacillus subtilis*," *Gene* (1981) 16:199.
Ruppen et al., "Efficient Expression of Human Growth Hormone in *Bacillus subtillis*," in Bacillus Molecular Genetics and Biotechnology Applications, eds. A. T. Garreson and J. A. Hock, pp. 423–432, Academic Press (1986).
Cornelis et al., "Cloning and Expression of *Bacillus coagulans* Amylase Gene in *Escherichia coli*," 1982, *Mol. Gen. Genetics* 186:507.
Palluck et al., "Artrial Natriuretic Factor," *Life Science*, 1985, 36:1415.
Gryczan et al., "Direct selection of recombinant plasmids in *Bacillus subtilis*," (1982) *Gene* 20:459.
Gryczan et al., "Construction and properties of chimeric plasmids in *Bacillus subtilis*" (1987) *PNAS* 75:1428.

*Primary Examiner*—Ricahrd A. Schwartz
*Assistant Examiner*—John L. LeGuyader

[57] ABSTRACT

A vector for high-level expression of a heterologous gene in Bacillus, including a DNA sequence which encodes all or part of the structural gene and contains the promoter and ribosome binding site of a *Bacillus coagulans* amylase gene; within or immediately downstream of the structural gene is a site for insertion of heterologous DNA; when inserted, the heterologous DNA is in the same translational reading frame as the amylase gene; the heterologous DNA thus is under control of the *B. coagulans* amylase gene regulatory elements and expressed at high levels. A signal-encoding sequence may be inserted independent of, or along with, the heterologous DNA leading to authentic secretion of the heterologous protein.

42 Claims, 13 Drawing Sheets

```
      -360         -350         -340         -330         -320         -310
       *            *            *            *            *            *
  G GAT CCA TGC GGC AAG CGT TAC CCA TCT CCC TCT CCT TCC TGC ACA TGC TCC CGT GAA CTT
      -300         -290         -280         -270         -260         -250
       *            *            *            *            *            *
    TAC CAG TAA ATT TTT CAT TGG TTC CCC ACC TTT TTT ACA GAC TTA TCA CTA TAT TAT TAT
      -240         -230         -220         -210         -200         -190
       *            *            *            *            *            *
    AGA TAA ACC GGC CAA ACA ACC AAA TCG GGG CGC AAA GGA GAG CCG GGG GCT GGA TTT AAA
      -180         -170         -160         -150         -140         -130
       *            *            *            *            *            *
    CCA TTT TTG GAA AAA CAA AAG GAA AAC CTG CTT GTA AAA AGA TGT TTT CGC GAA ACG AAA
      -120         -110         -100          -90          -80          -70
       *            *            *            *            *            *
    GCG GGA ATA GTA CCT TTG TTC TCT TCG CCT TTT GTC ATG CTT AAA ATC ATA ATT GAT TGA
       -60          -50          -40          -30          -20          -10
        *            *            *            *            *            *
     AAA TTT TTT CAT GTT CAC TTA TAC TAA ACG CAT CAA CTA TTA CTT CTT TTG GAA GGG GCA
         1           10           20           30           40           50
         *            *            *            *            *            *
     GTT TTC TTG GAA CGG AAT CAT ACA ATC ATG CAG TTT TTT GAA TGG AAT ACG CCA GCA GAC
         Leu Glu Arg Asn His Thr Ile Met Gln Phe Phe Glu Trp Asn Thr Pro Ala Asp
        60           70           80           90          100          110
         *            *            *            *            *            *
     GGC AGC CAT TGG AAC CGG CTG AAA GAA ATG GCG CCT GAA TTA AAG AAA AGC GGG ATT GAT
         Gly Ser His Trp Asn Arg Leu Lys Glu Met Ala Pro Glu Leu Lys Lys Ser Gly Ile Asp
```

FIG.1-1

```
-300                    -290            -280              -270            -260            -250
  *                       *               *                 *               *               *
TAC CAG TAA ATT TTT CAT TGG TTC CCC ACC TTT TTT ACA GAC TTA TCA CTA TAT TAT TAT

-240                    -230            -220              -210            -200            -190
  *                       *               *                 *               *               *
AGA TAA ACC GGC CAA ACA ACC AAA TCG GGG CGC AAA GGA GAG CCG GGG GCT GGA TTT AAA

-180                    -170            -160              -150            -140            -130
  *                       *               *                 *               *               *
CCA TTT TTG GAA AAA CAA GAA AAC CTG CTT GTA AAA AGA TGT TTT CGC GAA ACG AAA

-120                    -110            -100               -90             -80             -70
  *                       *               *                 *               *               *
GCG GGA ATA GTA CCT TTG TTC TCT TCG CCT TTT GTC ATG CTT AAA ATC ATA ATT GAT TGA

-60                     -50             -40               -30             -20             -10
  *                       *               *                 *               *               *
AAA TTT TTT CAT GTT CAC TTA TAC TAA ACG CAT CAA CTA TTA CTT CCT TTG GAA GGG GCA 1                      10              20                30              40              50
  *                       *               *                 *               *               *
GTT TTC TTG GAA CGG AAT CAT ACA ATC ATG CAG TTT TTT GAA TGG AAT ACG CCA GCA GAC
Met Glu Arg Asn His Thr Ile Met Gln Phe Phe Glu Trp Asn Thr Pro Ala Asp
```

|  | 60 | | 70 | | 80 | | 90 | | 100 | | 110 | |
|---|---|---|---|---|---|---|---|---|---|---|---|---|
|  | * | | * | | * | | * | | * | | * | |
| GGC | AGC | CAT | TGG | AAC | CGG | CTG | AAA | GAA | ATG | GCG | CCT | GAA | TTA | AAG | AAA | AGC | GGG | ATT | GAT |
| Gly | Ser | His | Trp | Asn | Arg | Leu | Lys | Glu | Met | Ala | Pro | Glu | Leu | Lys | Lys | Ser | Gly | Ile | Asp |

|  | 120 | | 130 | | 140 | | 150 | | 160 | | 170 | |
|---|---|---|---|---|---|---|---|---|---|---|---|---|
|  | * | | * | | * | | * | | * | | * | |
| GCC | GTC | TGG | CTT | CCG | GTG | ACA | AAA | GGA | CAG | TCA | GAC | ATG | GAC | AAT | GGT | TAC | GGG | GTG |
| Ala | Val | Trp | Leu | Pro | Pro | Val | Thr | Lys | Gly | Gln | Ser | Asp | Met | Asp | Asn | Gly | Tyr | Gly | Val |

|  | 180 | | 190 | | 200 | | 210 | | 220 | | 230 | |
|---|---|---|---|---|---|---|---|---|---|---|---|---|
|  | * | | * | | * | | * | | * | | * | |
| TAC | GAC | CAT | TAC | GAC | CTC | GGG | GAG | TTT | GAC | CAG | AAA | GGC | ACC | GTC | AGG | ACA | AAG | TAC | GGG |
| Tyr | Asp | His | Tyr | Asp | Leu | Gly | Glu | Phe | Asp | Gln | Lys | Gly | Thr | Val | Arg | Thr | Lys | Tyr | Gly |

|  | 240 | | 250 | | 260 | | 270 | | 280 | | 290 | |
|---|---|---|---|---|---|---|---|---|---|---|---|---|
|  | * | | * | | * | | * | | * | | * | |
| ACA | AAA | CAG | CAA | TTA | CAT | GAA | GCG | ATC | AAC | GCC | TGC | CAC | GAG | CAC | GAT | ATC | CAG | GTC | TAT |
| Thr | Lys | Gln | Gln | Leu | His | Glu | Ala | Ile | Asn | Ala | Cys | His | Glu | His | Asp | Ile | Gln | Val | Tyr |

FIG. 1-2  Nucleotide and amino acid sequence of the
B. coagulans amylase regulatory region Coding region of
B. coagulans amylase gene

FIG.6-1

```
       -360       -350       -340       -330       -320       -310
         *          *          *          *          *          *
G GAT CCA TGC GGC AAG CGT TAC CCA TCT CCC TCT CCC TGC ACA TGC TCC CGT GAA CTT
           -300       -290       -280       -270       -260       -250
             *          *          *          *          *          *
TAC CAG TAA ATT TTT CAT TGG TTC CCC ACC TTT TTT ACA GAC TTA TCA CTA TAT TAT TAT
           -240       -230       -220       -210       -200       -190
             *          *          *          *          *          *
AGA TAA ACC GGC CAA ACA ACC AAA TCG GGG CGC AAA GGA GAG CCG GGG GCT GGA TTT AAA
           -180       -170       -160       -150       -140       -130
             *          *          *          *          *          *
CCA TTT TTG GAA AAA CAA AAG GAA AAC CTG CTT GTA AAA AGA TGT TTT CGC GAA ACG AAA
           -120       -110       -100        -90        -80        -70
             *          *          *          *          *          *
GCG GGA ATA GTA CCT TTG TTC TCT TCG CCT TTT GTC ATG CTT AAA ATC ATA ATT GAT TGA
            -60        -50        -40        -30        -20        -10
             *          *          *          *          *          *
AAA TTT TTT CAT GTT CAC TTA TAC TAA ACG CAT CAA CTA TTA CTT CTT TTG GAA GGG GCA
              1         10         20         30         40         50
              *          *          *          *          *          *
GTT TTC TTG GAA CGG AAT CAT ACA ATC ATG CAG TTT TTT GAA TGG AAT ACG CCA GCA GAC
                         Leu Glu Arg Asn His Thr Ile Met Gln Phe Phe Glu Trp Asn Thr Pro Ala Asp
             60         70         80         90        100        110
              *          *          *          *          *          *
GGC AGC CAT TGG AAC CGG CTG AAA GAA ATG GCG CCT GAA TTA AAG AAA AGC GGG ATT GAT
Gly Ser His Trp Asn Arg Leu Lys Glu Met Ala Pro Glu Leu Lys Lys Ser Gly Ile Asp
```

FIG.6-2

Complete sequence of the B. coagulans amylase gene

```
         120         130         140         150         160         170
          *           *           *           *           *           *
GCC GTC TGG CTT CCG GTG ACA AAA GGA CAG TCA GAC ATG GAC AAT GGT TAC GGG GTG
Ala Val Trp Leu Pro Val Thr Lys Gly Gln Ser Asp Met Asp Asn Gly Tyr Gly Val 180         190         200         210         220         230
          *           *           *           *           *           *
TAC GAC CAT TAC GAC CTC GGG GAG TTT GAC CAG AAA GGC ACC GTC AGG ACA AAG TAC GGG
Tyr Asp His Tyr Asp Leu Gly Glu Phe Asp Gln Lys Gly Thr Val Arg Thr Lys Tyr Gly 240         250         260         270         280         290
          *           *           *           *           *           *
ACA AAA CAG CAA TTA CAT GAA GCG ATC AAC GCC TGC CAC GAG CAC GAT ATC CAG GTC TAT
Thr Lys Gln Gln Leu His Glu Ala Ile Asn Ala Cys His Glu His Asp Ile Gln Val Tyr 300         310         320         330         340         350
          *           *           *           *           *           *
ATC GAT GTC GTC ATG GTG AAC CAT AAA GCG GGC GCG GAT GAA ACC GAA TCT TTC CAA GTG GTG
Ile Asp Val Val Met Val Asn His Lys Ala Gly Ala Asp Glu Thr Glu Ser Phe Gln Val Val 360         370         380         390         400         410
          *           *           *           *           *           *
GAG GTC GAC CCG ATG GAC CGC AAC GAC CGC AAC AAA GAA ATT TCC GAA CCG TTT GAA ATA GAA GGC TGG
Glu Val Asp Pro Met Asp Arg Asn Asp Arg Asn Lys Glu Ile Ser Glu Pro Phe Glu Ile Glu Gly Trp
```

FIG.6-3

```
420         430         440         450         460         470
 *           *           *           *           *           *
ACA AAG TTC AAT TTT ACA AAC CGG AAG TAT TCT GAT TTT ACG TGG AAT CAT ACC
Thr Lys Phe Asn Phe Thr Asn Arg Lys Tyr Ser Asp Phe Thr Trp Asn His Thr 480         490         500         510         520         530
 *           *           *           *           *           *
CAT TTC AGT GGC GTC GAT TAC GAC AAC CGG ACA AAC GGC ATT TTC CGT ATT GTC
His Phe Ser Gly Val Asp Tyr Asp Asn Arg Thr Asn Gly Ile Phe Arg Ile Val 540         550         560         570         580         590
 *           *           *           *           *           *
GGG GAA AAT AAG CAT TGG AGT GAG CAT GTC GAC AAC GAA TTT GGA AAC TTC GAT TAT TTG
Gly Glu Asn Lys His Trp Ser Glu His Val Asp Asn Glu Phe Gly Asn Phe Asp Tyr Leu 600         610         620         630         640         650
 *           *           *           *           *           *
ATG TAC GCG GAC ATT GAT TAC AAC CAT CCG GAT GTA AAA AAA GAA ATG ATC GAA TGG GGA
Met Tyr Ala Asp Ile Asp Tyr Asn His Pro Asp Val Lys Lys Glu Met Ile Glu Trp Gly 660         670         680         690         700         710
 *           *           *           *           *           *
AAA TGG CTG GCC GAT ACG ACC GGT TGC GAC GGC TAC CGG CTC GAT GCC ATT AAG CAT ATC
Lys Trp Leu Ala Asp Thr Thr Gly Cys Asp Gly Tyr Arg Leu Asp Ala Ile Lys His Ile 720         730         740         750         760         770
 *           *           *           *           *           *
AAC CAT GAC TTT ATC CGC GAC TTT GCC GCT GCC TTA ATG GAA CAC CGC GGA GAC CAT TTT
Lys Trp Leu Ala Asp Thr Thr Gly Cys Asp Gly Tyr Arg Leu Asp Ala Ile Lys His Ile 780         790         800         810         820         830
 *           *           *           *           *           *
TAT TTT GTC GGC GAG TTC TGG AAT CCG CAG CTG GAA GCG TGC CAA AAA TAC CTC GAC CAT
Tyr Phe Val Gly Glu Phe Trp Asn Pro Gln Leu Glu Ala Cys Gln Lys Tyr Leu Asp His
```

```
       840                850                860                870                880                890
        *                  *                  *                  *                  *                  *
GTA CAG TTT AAA ATC GAT TTC GAT GTT GCA CTC CAT TAT AAA TTG CAT GAA GCA TCT
Val Gln Phe Lys Ile Asp Phe Asp Val Ala Leu His Tyr Lys Leu His Glu Ala Ser 900                910                920                930                940                950
        *                  *                  *                  *                  *                  *
AAA AAA GGG CGC GCG TTT GAC CTC CCG ACG ATT TTT CAT GAT ACA CTC GTT CAA ACG CAC
Lys Lys Gly Arg Ala Phe Asp Leu Pro Thr Ile Phe His Asp Thr Leu Val Gln Thr His 960                970                980                990               1000               1010
        *                  *                  *                  *                  *                  *
CCG CTG AAT GCT GTT ACG TTT GTC GAT AAC CAT GAT TCA CAG CCG AAC GAA TCG CTG GAA
Pro Leu Asn Ala Val Thr Phe Val Asp Asn His Asp Ser Gln Pro Asn Glu Ser Leu Glu 1020               1030               1040               1050               1060               1070
        *                  *                  *                  *                  *                  *
TCA TGG GTG GAC GAC TGG TTT AAG CAG AGC GCC TAT GCC TTG ATT CTG CTG CGG AAA GAC
Ser Trp Val Asp Asp Trp Phe Lys Gln Ser Ala Tyr Ala Leu Ile Leu Leu Arg Lys Asp 1080               1090               1100               1110               1120               1130
        *                  *                  *                  *                  *                  *
GGT TAT CCG TGC GTC TTT TAC GGG GAT ATG TAC GGC ATC GGC GAC AAT CCG ATT CCC
Gly Tyr Pro Cys Val Phe Tyr Gly Asp Met Tyr Gly Ile Gly Asp Asn Pro Ile Pro 1140               1150               1160               1170               1180               1190
        *                  *                  *                  *                  *                  *
GGA AAA AAA GAC GCC CTT TCC CCG CTT TTA TCT GTC CGG CGG GAA AAA GCG TAT GGC GAG
Gly Lys Lys Asp Ala Leu Ser Pro Leu Leu Ser Val Arg Arg Glu Lys Ala Tyr Gly Glu
```

FIG.6-4

```
              1200                1210                1220                1230                1240                1250
               *                   *                   *                   *                   *                   *
CAA GAT GAT TAT TTC GAC CAT CCG AAC ACA ATC GGC TGG GTG CGC CGC GGC GTT CCG GAG
Gln Asp Asp Tyr Phe Asp His Pro Asn Thr Ile Gly Trp Val Arg Arg Gly Val Pro Glu 1260                1270                1280                1290                1300                1310
               *                   *                   *                   *                   *                   *
ATC CCG CAT TCC GGC TGT GCC GTC GTT ATC TCA AAC GGC GAG AAC AAA AGA ATG
Ile Pro His Ser Gly Cys Ala Val Val Ile Ser Asn Gly Glu Asn Lys Arg Met 1320                1330                1340                1350                1360                1370
               *                   *                   *                   *                   *                   *
CTT GTC GGA AAA GAG CGC GCT GGC GAG GTT TGG GTG GAC GCT ACC GGC AAC CGG CAG GAA
Leu Val Gly Lys Glu Arg Ala Gly Glu Val Trp Val Asp Ala Thr Gly Asn Arg Gln Glu 1380                1390                1400                1410                1420                1430
               *                   *                   *                   *                   *                   *
AAA GTT ACA ATT GGC GAA GAC GGC TAT GCA GGA TTT CCG GTT AAC GGC GGC AGC GTT TCT
Lys Val Thr Ile Gly Glu Asp Gly Tyr Ala Gly Phe Pro Val Asn Gly Gly Ser Val Ser 1440                1450                1460                1470                1480                1490
               *                   *                   *                   *                   *                   *
GTC TGG GTA CAG GAA ACG GAT GAA AAC TAA GGA GGG GCA CTG TTC CAT CTT CCG GAA CGG
Val Trp Val Gln Glu Thr Asp Glu Asn ---
```

FIG.6-5

```
        1500      1510      1520      1530      1540      1550
         *         *         *         *         *         *
TGC TTA TTT CAT TCT TTC AGC TTA TAG CTG TTT TTG CCG CGT TTT TTA ATT TCG TAC ATC
        1560      1570      1580      1590      1600      1610
         *         *         *         *         *         *
GTT TCA TCC GCT TTT GCA ATC AAG GTT TCT TCA TCG CTG CAA TGG TCC GGA TAC AAA CTG
        1620      1630      1640      1650      1660      1670
         *         *         *         *         *         *
ATC AAC TTA ACA AAA ATC CAT CAA GTC GAA GAC ATA TTA CAT CTT TAT GGA ACA TTC ATG
        1680      1690      1700      1710      1720      1730
         *         *         *         *         *         *
ACC TTG ATG AAA TGG CAC TAA ATC CTT GTG TTT GGA ATA CTC AAT GGC TTG TAA AAG AAG
        1740      1750      1760      1770      1780      1790
         *         *         *         *         *         *
GAA GTC TTC ATT TGA TTG TTG GAG TCC GTT AAT TAG TAG CGG CTT TAG GGA GTA ATC CCT
        1800      1810
         *         *
ATC GAA TAA ATC TGT GAA TTC
```

```
                    10v         20v         30v
B.licheniformis     MKQQKRLYARLLTLLFALIFLLPHSAAAANLNGT
                                             .. N T
B.coagulans                                  LER NHT 40v         50v         60v         70v         80v         90v
B.licheniformis     LMQYFEWYMPNDGQHWKRLQNDSAYLAEHGITAVWIPPAYKGTSQADVGYGAYDLYDLGE
                    :MQ:FEW  P.DG HW:RL::  ::  L . GI.AVW:PP.  KG S:  D GYG YD YDLGE
B.coagulans         IMQFFEWNTPADGSHWNRLKEMAPELKKSGIDAVWLPPVTKGQSDMDNGYGVYDHYDLGE 100v        110v        120v        130v        140v        150v
B.licheniformis     FHQKGTVRTKYGTKGELQSAIKSLHSRDINVYGDVVINHKGGADATEDVTAVEVDPADRN
                    F:QKGTVRTKYGTK :L:.AI::  H.:DI:VY DVV:NHK:GAD.TE.  .VEVDP DRN
B.coagulans         FDQKGTVRTKYGTKQOQHEAINACHEHDIQVYIDVVMNHKAGADETESHQVVEVDPMDRN 160V        170V        180V        190V        200V        210V
B.licheniformis     RVISGEHLIKAWTHFHFPGRGSTYSDFKWHWYHFDGTDWDESRKLNRIYKFQGKAWDW--
                    : IS.   I.:WT.F:F:F..R  :.YSDF.W:   HF.G.D.D:.   N I:::  G.. :W
B.coagulans         KEISEPFEIEGWTKFNFTNRKGKYSDFTWNHTHFSGVDYDNRTGRNGIFRIVGENKHWSE 220v        230v        240v        250v        260v        270v
B.licheniformis     EVSNENGNYDYLMYADIDYDHPDVAAEIKRWGTWYANELQLDGFRLDAVKHIKFSFLRDWV
                    :V.NE GN:DYLMYADIDY:HPDV   E:  WG.W A:.    DG:RLDA:KHI:  .F:RD..
B.coagulans         HVDNEFGNFDYLMYADIDYNHPDVKKEMIEWGKWLADTTGCDGYRLDAIKHINHDFIRDFA
```

```
                    280v          290v          300v          310v          320v          330v
B.licheniformis  NHVREKTGKEMFTVAEYWQNDLGALENYLNKTNFNHSVFDVPLHYQFHAASTQGGYDMRK
                 .:E. G.:.: V:E:W: :L.A ::YL:...:F: .:FDV:LHY::H.AS.:G ::D:..
B.coagulans      AALMEHRGDHFYFVGEFWNPQLEACQKYLDHVQFKIDLFDVALHYKLHEASKKGRAFDLPT 340v          350v          360v          370v          380v          390v
B.licheniformis  LLNGTVVSKHPLKSVTFVDNHDTQPGQSLESTVQTWFKPLAYAFILTRESGYPQVFYGDM
                 ::::T:V .HPL::VTFVDNHD:QP.:SLES V:.WFK. AYA:IL R..GYP VFYGDM
B.coagulans      IFHDTLVQTHPLNAVTFVDNHDSQPNESLESWVDDWFKQSAYALILLRKDGYPCVFYGDM 400v          410v          420v          430v          440v          450v
B.licheniformis  YGTKGDSQREIPALKHKIEPILKARKQYAYGAQHDYFDHHDIVGWTREGDSSVANSGLAA
                 YG. GD . IP: K: ..P:L..R:: AYG.Q:DYFDH.:.:GW.R G :.::: SG A.
B.coagulans      YGIGGD--NPIPGKKDALSPLLSVRREKAYGEQDDYFDHPNTIGWVRRGVPEIPHSGCAV 460v          470v          480v          490v          500v          510v
B.licheniformis  LITDGPGGAKRMYVGRQNAGETWHDITGNRSEPVVINSEGWGEFHVNGGSVSIYVQRX
                 :I::G .G.KRM VG::.AGE.W D TGNR E V.I..:G..:F.VNGGSVS:.VQ .
B.coagulans      VISNGENGEKRMLVGKERAGEVWDATGNRQEKVTIGEDGYAGFPVNGGSVSVWVQETDENX
```

FIG.7-2    Comparison of the amino acid sequences of the amylase genes from B.licheniformis and B.coagulans

EXPRESSION OF HETEROLOGOUS DNA USING THE *BACILLUS COAGULANS* AMYLASE GENE

BACKGROUND OF THE INVENTION

This invention relates to the use of genetic engineering to produce desired heterologous polypeptides. (As used herein, "polypeptides" means any useful chain of amino acids, including proteins and peptides, and "heterologous" means a polypeptide not naturally produced by the host cell which produces the polypeptides.)

Bacillus strains have been used as hosts to produce heterologous polypeptides encoded on genetically engineered vectors. The use of a Gram positive Bacillus cell as host avoids some problems associated with expressing heterologous genes in Gram negative organisms such as *E. coli;* for example, problems associated with the production of endotoxins.

A number of Bacillus expression systems have been reported wherein heterologous proteins can be produced using a variety of cloned regulatory elements.

Hardy et al. (Nature, 1981, 293:481 and EP Application No. 82302157.1) expressed DNA sequences encoding the core antigen of hepatitis B virus and the major antigen of foot and mouth disease virus in *Bacillus subtilis* using the erythromycin resistance gene promoter on plasmid pBD9.

Williams et al. (Gene, 1981, 16:199) expressed the mouse dihydrofolate reductase gene in *Bacillus subtilis* using the vector pPL608, containing a phage SP02 promoter.

Ruppen et al. (in "Bacillus Molecular Genetics and Biotechnology Applications", eds. A. T. Garreson and J. A. Hoch, pp 423–432, Academic Press 1986) reported the use of the hybrid spac-1 promoter, a synthetic ribosome binding site, and the *E. coli lpp* gene terminater to produce recombinant human growth hormone in *B. subtilis.*

SUMMARY OF THE INVENTION

The invention provides an improved expression system for the production of heterologous polypeptides in Gram positive bacteria such as *B. subtilis.* The invention makes use of our isolation of, and discoveries regarding, a gene encoding a novel amylase of *Bacillus coagulans,* which is expressed at unusually high levels. According to the invention, DNA encoding a desired heterologous polypeptide is positioned in a vector so as to be under the control of the *B. coagulans* amylase regulatory region, to effect high level expression of the polypeptide. (*B. coagulans* is available from the American Type Culture Collection, Rockville, Md., Accession No. 23498.)

The novel amylase gene of *Bacillus coagulans,* in addition to being expressed at unusually high levels in *B. subtilis* when carried on a plasmid vector, is unique among genes encoding exported amylases, e.g., amylase genes of *B. licheniformis, B. amyloliquefaciens, B. stearothermophilus* and *B. subtilis,* in that it also lacks a signal peptide encoding sequence. As such, this novel amylase gene is not the amylase gene of Cornelis et al., 1982, Mol. Gen. Genetics 186:507. The amylase that Cornelis et al. describe appears to be similar if not identical to an amylase from *B. licheniformis,* and in fact the authors state that the strain may be *B. licheniformis.* We have discovered that, despite the lack of a signal peptide encoding sequence on the *B. coagulans* amylase gene, considerable levels of amylase are ultimately found extracellularly, presumably because of the abundance of protein produced and the release of this protein by the cell. We have further discovered that a heterologous gene, when genetically engineered so as to be under the transcriptional and translational control of the *B. coagulans* regulatory region, is also expressed in large amounts.

In addition to the regulatory region of the *B. coagulans* gene, the vector of the invention advantageously includes all or part of the amylase structural gene; preferably the portion of the structural gene encodes either at least the first (amino terminal) 2 or 30 amino acids of amylase. The vector also preferably includes, downstream of and in reading frame with the regulatory region, a site for insertion of heterologous DNA, so that the DNA is under the transcriptional control of the *B. coagulans* promoter. This site is most preferably located within or at the 3' end of the amylase structural gene, immediately upstream from the translation stop codon, so that expression produces a fusion protein (all or a portion of *B. coagulans* amylase fused to the desired heterologous polypeptide), in which the partial or complete amylase protein serves as a protective carrier for stabilization against protease degradation of the heterologous polypeptide. This stabilization is particularly important for peptides and small polypeptides, and eukaryotic proteins, which can otherwise be substantially degraded by host cell proteases.

In another preferred embodiment, a signal peptide encoding sequence is inserted upstream of the heterologous gene and downstream of the amylase regulatory region, or portion of the structural gene; the signal peptide encoding sequence is one capable of functioning in Gram positive, preferably Bacillus, host cells, and thus effecting secretion of the heterologous gene product. Preferably the signal peptide encoding sequence is derived from a Bacillus species, most preferably from a Bacillus protease gene, such as the *B. subtilis* subtilisin gene described in Sloma et al. (U.S. application Ser. No. 921,343, assigned to the same assignee and hereby incorporated by reference), the *B. cereus* penicillinase gene described in Sloma et. al., (U.S. Pat. No. 4,633,280), the *B. licheniformis* penicillinase gene described in Chang et. al., (U.S. Pat. No. 4,711,844), the *B. subtilis* alpha-amylase gene described in Yamane et. al., (U.S. Pat. Nos. 4,690,898 and 4,663,294), or the *B. licheniformis* alpha-amylase gene described in Stephens et. al., (U.S. application Ser. No. 845,864, assigned to the same assignee and hereby incorporated by reference).

In another preferred embodiment, the host cell is a Gram positive cell, preferably a Bacillus cell of the species *B. subtilis* or, alternatively, from one of the species *B. licheniformis, B. amyloliquefaciens, B. polymyxa, B. stearothermophilus, B. thermoproteolyticus, B. coagulans, B. thuringiensis, B. megaterium, B. cereus, B. natto,* or *B. acidocaldarius.*

Examples of heterologous DNA which can be expressed according to the invention include any desired polypeptide, e.g., medically useful proteins such as hormones, vaccines, antiviral proteins, antitumor proteins, antibodies, or clotting proteins, and agriculturally and industrially useful proteins such as enzymes or pesticides. One example of a desired eukaryotic protein which can be expressed according to the invention is atrial natriuretic factor. This factor has been reported in the literature under a variety of names, and as having a range of amino acid chain lengths; these are given in Palluk et al., Life Sciences, 1985, 36:1415. Herein there is used the nomenclature of FIG. 1 of that paper, which names the precursor molecule atrial natriuretic factor and three smaller biologically active fragments of the molecule, Atriopeptin I, Atriopeptin II, and Atriopeptin III ("APIII"). These peptides can be administered to human patients to control hypertension and regulate serum sodium and potassium levels.

Other features and advantages of the invention will be apparent from the following description of the preferred embodiments thereof, and from the claims.

DESCRIPTION OF THE PREFERRED EMBODIMENTS

The drawings will first be briefly described.

Drawings

FIG. 1 (parts 1 and 2) is the nucleotide and amino acid sequence of the 5' terminus of the *B. coagulans* amylase gene.

FIG. 6 (parts 1-6) is the nucleotide and amino acid sequence of the entire *B. coagulans* amylase gene.

FIG. 7 (parts 1 and 2) is a comparison of the amino acid sequences of the amylase genes of *B. licheniformis* and *B. coagulans*.

CONSTRUCTION OF VECTORS

Figure 2:
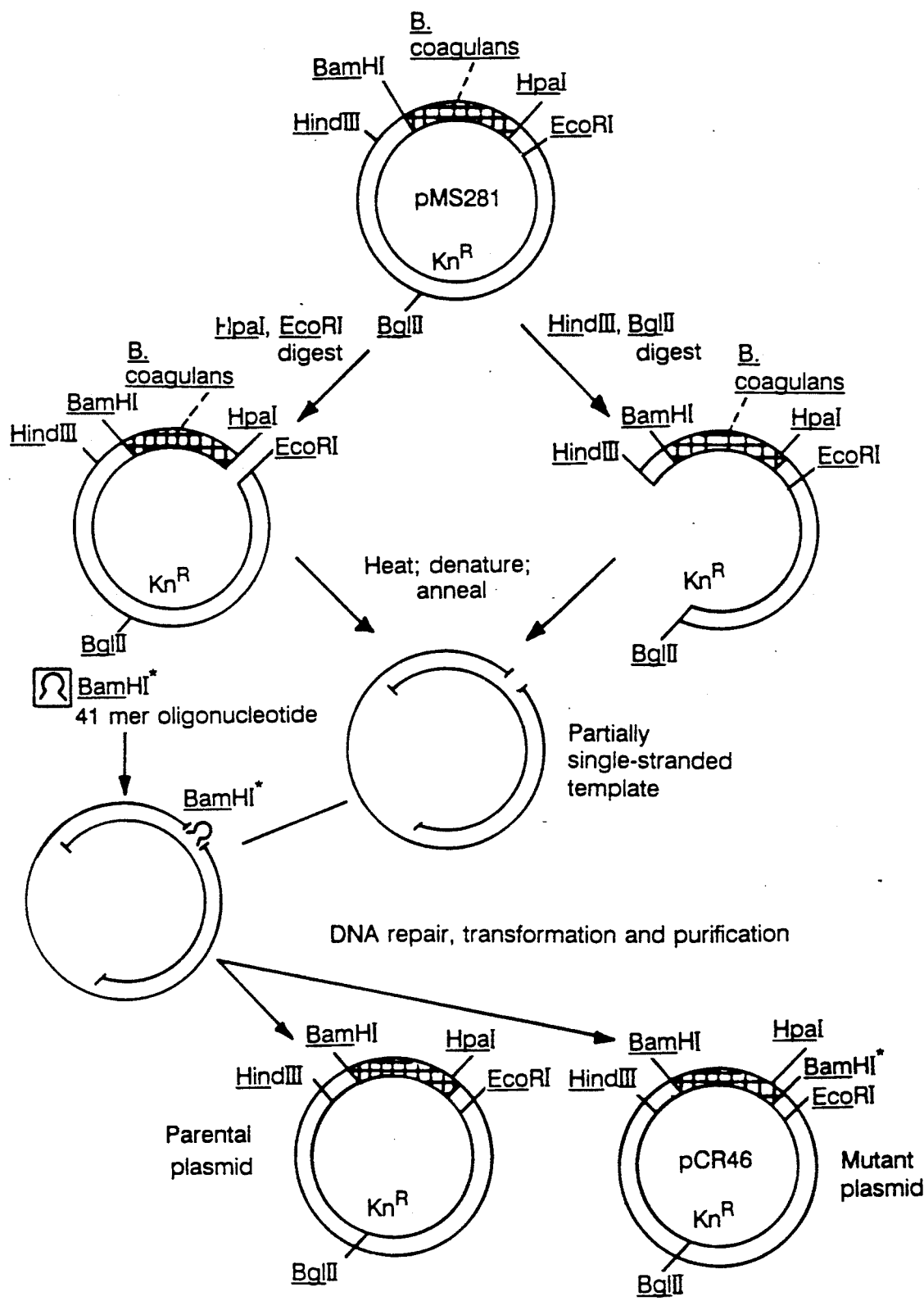
FIG. 2 is a diagrammatic representation of the construction of an intermediate vector containing the *B. coagulans* amylase gene with a downstream BamHI site.
Figure 3:
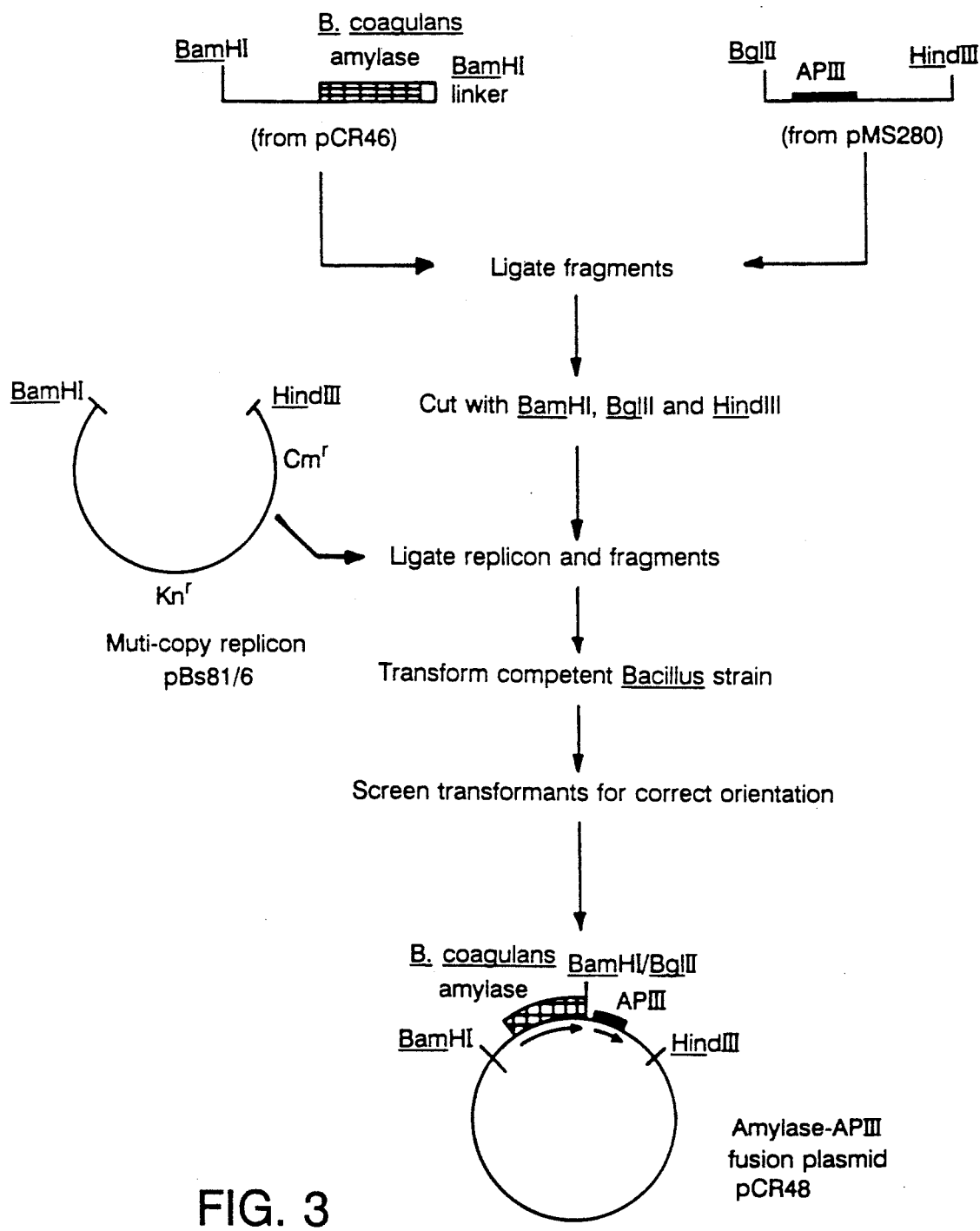
FIG. 3 is a diagrammatic representation of the construction of vector pCR48, containing the *B. coagulans* amylase gene sequence and the APIII gene.
Figure 4:
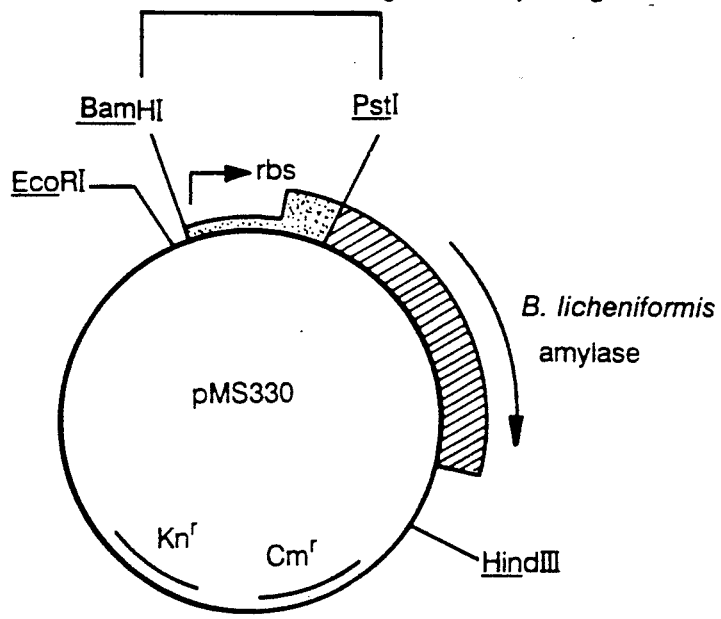
FIG. 4 is a diagrammatic representation of vector pMS330 containing the *B. coagulans* amylase regulatory region and the *B. licheniformis* amylase gene.

Two vectors of the invention, pCR48 and pMS330, are illustrated in FIGS. 3 and 4. The first step in their construction was the isolation of the *B. coagulans* amylase gene from a DNA library, as follows.

Cloning the Amylase Gene from *B. coagulans*

Chromosomal DNA was isolated from *B. coagulans* strain A.T.C.C. Accession No. 23498, partially digested with Sau3A, and size fractionated by electrophoresis on a 0.8% agarose gel. DNA in the 3-6 kb size range was electroeluted from the gel. This DNA was ligated to BclI-cut pBD214 (Gryczan et al., 1982, Gene 20:459) at a 2:1 ratio of chromosomal DNA to vector DNA. The ligated DNA was then transformed into competent cells of *B. subtilis* BD393 (Gryczan et al., supra), resulting in 7200 $Tmp^R$ $CM^R$ colonies ("$Tmp^R$" is trimethoprim resistant; "$Cm^R$" is chloramphenicol resistant). Three out of 3350 $Tmp^R$ $Cm^R$ colonies formed halos when plated on starch-azure indicator plates. Plasmid DNA from all three of these colonies was able to transform a different amylase-minus *B. subtilis* strain to Amy+, indicating that an amylase gene had been cloned on these plasmids. One colony produced a large halo and contained a plasmid (pNH237) with an insert size of approximately 3.8 kb.

Expression of *B. coagulans* Amylase in *B. subtilis*

Plasmid pNH237 was transformed into a protease deficient and sporulation-minus *B. subtilis* host strain designated GP205 (aprΔ, nprΔ, spoOA). Cultures of GP205 containing pNH237 were grown overnight in LB containing chloramphenicol (5 ug/ml), and samples of supernatant fractions were analyzed by SDS-polyacrylamide gel electrophoresis with Coomassie Brilliant Blue staining. For comparison purposes, samples of supernatant fluids from cultures of GP205 containing a cloned *B. licheniformis* amylase gene were also run on the same gels. (This gene, and the use of its signal peptide encoding sequence in secretion vectors, has been described in Stephens et al., U.S. Ser. No. 845,864, assigned to the same assignee and hereby incorporated by reference).

Cells containing the *B. coagulans* amylase gene (on pNH237) were found to synthesize large amounts of a protein of MW approximately 59,000. Comparison of densitometric quantitations of protein bands in a polyacrylamide gel showed that cells containing pNH237 produced 5-10 fold more amylase protein than cells containing the *B. licheniformis* amylase gene carried on the same vector. Additional data indicated that the significantly more amylase protein than the *B. amyloliquefaciens* amylase gene carried on the same vector.

The location of the amylase gene on pNH237 was determined, its nucleotide sequence obtained, and its associated regulatory sequences identified as described below.

Localization of the *B. coagulans* Amylase Gene

Figure 5:
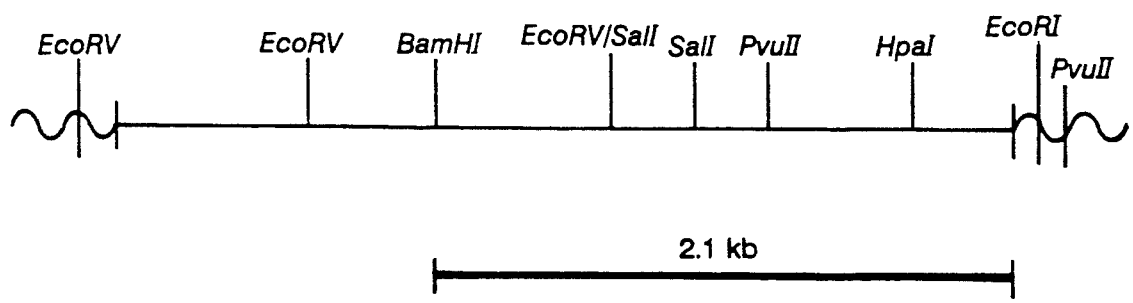
FIG. 5 is a restriction map of the portion of the *B. coagulans* DNA sequence containing the amylase gene, in a *B. subtilis* vector.

To determine where the coding region of the gene is located within the 3.8 kb insert of pNH237, a restriction map of this DNA was generated (FIG. 5). By constructing plasmids that were deleted for either one or both of the two EcoRV fragments, it was determined that the presence of the 1.25 kb EcoRV fragment was essential for amylase activity and that the 1.0 kb EcoRV fragment could be eliminated without affecting activity; information essential for amylase expression must therefore lie within the 1.25 kb central EcoRV fragment.

To more precisely map the gene, the plasmid DNA was used to direct the synthesis of amylase in an in vitro transcription/translation system. The plasmid DNA was cleaved with various restriction enzymes to determine which restriction sites lie within the gene (cleavage at sites within the gene disrupt the synthesis of the product). Uncut DNA, and DNA which was not cleaved within the insert (EcoRI), produced a protein of MW of about 59,000. Restriction of the DNA with either PvuII, EcoRV, or SalI eliminated synthesis of the 59 Kd protein, indicating that those enzymes cut within the coding sequence, while cleavage with BamHI did not affect synthesis of the protein. The gene was thus localized to the approximately 2.1 kb portion of the insert between the BamHI site and the end of the insert (FIG. 5). This fragment was removed from pNH237 on the 2.1 kb EcoRI - BamHI fragment and cloned into EcoRI/BamHI-digested pBs81/6. (pBs81/6 is a multicopy plasmid that is derived from pBD64 (Gryczan et al., 1978, PNAS 75:1428), a standard Bacillus cloning vector, by changing the PvuII site to a HindIII site with a synthetic linker.) The resulting plasmid is designated pMS281.

Sequence of the *B. coagulans* Amylase Gene

The entire 2.1 kb of DNA between the BamHI and EcoRI sites of pMS281 was sequenced by the Sanger dideoxy method. The nucleotide sequence of the entire amylase gene is given in FIG. 6.

The *B. coagulans* amylase gene has significant homology with the alpha-amylase genes of *B. stearothermophilus* (58%) and *B. licheniformis* (62%). The region of homology begins immediately after the signal peptide encoding sequence for the *B. licheniformis* gene and corresponds to the 5' end of the coding region for the *B. coagulans* amylase gene (FIG. 7). The *B. coagulans* gene does not have an open reading frame 5' to the region of homology with the *B. licheniformis* amylase, and the deduced N-terminal amino acid sequence of the protein does not resemble a typical signal peptide sequence, indicating that *B. coagulans* amylase is not associated with a conventional signal peptide sequence.

The amino acid sequence of purified *B. coagulans* amylase was determined, and found to correspond to that predicted by the DNA sequence, except for the presence of an N-terminal methionine residue (normally encoded by ATG) in place of the predicted leucine residue (encoded by TTG). This is explained by the fact that TTG is known to sometimes encode the N-terminal methionine in Gram positive organisms.

Sequences resembling RNA polymerase and ribosome binding sites were found at the appropriate positions upstream from the TTG initiation codon. The sequence TTGAAA at position -70 closely resembles the canonical -35 region (TTGACA) for *B. subtilis* promoters recognized by the sigma[43]-RNA polymerase, and the sequence TATACT (position -47 closely resembles the canonical -10 region (TATAAT) for *B. subtilis* sigma[43] promoters. The TTG initiation codon is preceded by the sequence GAAGGGG (position -15), which could function as a Bacillus ribosome binding site.

CONSTRUCTION OF FUSION VECTORS

Two approaches were used to construct fusion vectors. The first approach involved igonucleotide-directed mutagenesis of the 3' end of the *B. coagulans* amylase gene to introduce a BamHI site, for the insertion of the gene encoding APIII, in frame with a full-length copy of the *B. coagulans* amylase gene. The second approach involved the fusion of a heterologous gene to the regulatory region of the *B. coagulans* amylase gene to demonstrate that region's ability to direct expression of a heterologous polypeptide. The former approach yielded plasmid pCR48 (FIG. 3), and the latter plasmid pMS330.

pCR48

FIG. 3 is a diagrammatic representation of pCR48, a vector in which DNA encoding APIII is inserted adjacent to the 3' end of the *B. coagulans* amylase gene, such that an amylase-APIII fusion protein is expressed under the transcriptional and translational control of the *B. coagulans* amylase promoter and ribosome binding sequence. pCR48 was constructed as follows.

A BamHI site was inserted at the 3' end of the amylase gene in pMS281 using oligonucleotide-directed mutagenesis. A 41 base oligomer, complementary to the nucleotide sequence of either side of the amylase stop codon and containing 6 additional bases encoding a BamHI recognition site, was introduced between the last codon and the stop codon of the amylase gene. The nucleotide sequence of the oligomer is as follows:

5'
GGTACAGGAAACGGATGAAAACG-
GATCCTAAGGAGGGGCAC 3'.

Insertion of the oligomer resulted in the addition of two corresponding amino acids encoded within the BAMHI site (glycine and serine) at the C-terminus of the amylase polypeptide. The strategy for inserting the BamHI site was as follows.

Samples of plasmid pMS281 (containing the entire amylase gene) were digested with HpaI and EcoRI (to delete the region of DNA that included the 3' terminus of the amylase gene) or HindIII and BqlII (to inactivate the kanamycin resistance gene). The samples were mixed, the plasmids were denatured, and single strands were allowed to reanneal in the presence of the synthetic oligomer. The oligonucleotide annealed with the single stranded region of the template that was created by restriction enzyme digestion of the plasmid of the complementary strand; it was incorporated into the plasmid by treating with DNA polymerase, in the presence of all four deoxynucleotides, to fill in the gaps. The mutagenized DNA was used to transform *B. subtilis* protoplasts, and transformants were selected by chloramphenicol resistance and the ability to synthesize amylase. The resultant plasmids were screened for the presence of the new BamHI site at the end of the amylase gene. The addition of the glycine and serine residues to the carboxy-terminus of the protein did not appear to affect amylase activity. One of these plasmids, pCR46, was used for the construction of gene fusions. (pCR46 has been deposited with the American Type Culture Collection, Accession No. 67736, and assigned to the same assignee).

The gene encoding APIII (see Stephens et al., supra) was inserted in-frame with the *B. coagulans* amylase gene at the newly created BamHI site by the following procedure. A BglII-HindIII fragment of DNA isolated from the plasmid pMS280, which contains the coding region for APIII located upstream of a segment of DNA derived from the 3' end of the *B. licheniformis* amylase gene, was ligated with the BamHI fragment from pCR46 containing the *B. coagulans* amylase gene. Cleavage with BamHI, BglII, and HindIII released fragments containing single copies of the *B. coagulans* amylase APIII fusion and having BamHI-HindIII ends. These fragments were then ligated with BamHI/HindIII-digested pBs81/6 (described supra.) and transformed into *B. subtilis*. The resulting plasmid was designated pCR48.

*B. subtilis* GP205 cells containing pCR48 were grown in liquid medium, and the contents of the cells and the spent culture fluid were analyzed separately for the presence of amylase or the amylase-APIII fusion protein. Cellular or extracellular protein was separated by size using SDS-polyacrylamide gel electrophoresis and visualized either by staining with Coomassie Brilliant Blue dye or by Western blot analysis using amylase-specific antibodies. A large quantity of amylase APIII fusion protein was produced in these cells and a significant portion of it (up to 50%) was released into the culture medium. This level of protein production was 5-10 fold greater than that of a fusion of the *B. licheniformis* amylase gene to the APIII gene.

The *B. coagulans* amylase regulatory region present on pCR48 is thus capable of directing the expression of high levels of fusion protein, the desired portion of which can be released and isolated from the purified fusion protein by cleavage with a suitable proteolytic reagent such as *Staphylococcus aureus* V8 protease (Mai et al., EP 0207044).

As mentioned above, DNA coding for other commercially useful heterologous polypeptides can also be inserted into or fused to the carboxy-terminus of the *B. coagulans* amylase gene to produce high levels of the corresponding heterologous polypeptide. In the case of the production of fusion proteins containing heterologous peptides for use as components of vaccines, it may not be necessary to purify the heterologous peptide away from the amylase carrier moiety of the fusion protein, as the fusion protein itself may be useful as a vaccine.

pMS330

FIG. 4 depicts pMS330, a vector in which the *B. coagulans* amylase gene and regulatory elements are inserted upstream of, and in the same translational reading frame as, the *B. licheniformis* amylase gene. The hybrid protein thus encoded is under the transcriptional and translational control of the *B. coagulans* amylase gene regulatory elements. This vector was constructed as follows.

Plasmid pMS283 (containing the *B. coagulans* amylase gene) was cut with BamHI and EcoRV and the 650bp fragment containing the regulatory region and the 5' end of the *B. coagulans* amylase gene was cloned between the BamHI and HincII sites of pUC18 to form pAS40. pAS40 was cut with NarI, treated with Klenow fragment of DNA polymerase in the presence of all four deoxynucleotides to create blunt ends, and ligated to a PstI linker (d[p'GCTGCAGC]). Following cleavage with BamHI and PstI, the 460 bp BamHI-PstI fragment containing the regulatory elements and approximately 30 codons of the *B. coagulans* amylase coding region was cloned into BamHI and PstI digested pBs92/13. (pBs92/13 carries the coding region of the *B. licheniformis* amylase gene but lacks the promoter and signal peptide encoding sequence.) This resulted in the placement of the *B. coagulans* amylase regulatory region upstream of a promoter-less and signal-less *B. licheniformis* amylase gene in pMS330.

After transformation into B. subtilis GP205 cells the fusion polypeptide produced by cells carrying pMS330 was analyzed. Most of the fusion protein produced remained cell associated. Cell associated proteins were extracted according to conventional procedures and analyzed by gel staining and Western blotting. The level of production of the *B. coagulans* amylase-*B. licheniformis* amylase fusion protein was less than that of wild type *B. coagulans* amylase, but considerably more than the level of amylase production seen with the *B. licheniformis* amylase gene alone. This confirmed that the regulatory elements and the promoter - proximal end of the *B. coagulans* gene are useful for directing high-level expression of a heterologous gene.

CONSTRUCTION OF SECRETION VECTORS

The expression vectors of the invention can be converted to secretion vectors by the addition of an efficient signal peptide encoding sequence. This is achieved either by introducing an efficient signal peptide encoding sequence into the *B. coagulans* amylase gene, or by using a heterologous gene which carries its own signal encoding DNA. An efficient signal peptide encoding sequence is introduced immediately downstream of the *B. coagulans* amylase gene, or fragment thereof, by inserting either a synthetic or a cloned copy of signal encoding DNA. The signal peptide encoding sequence derived from the *B. subtilis* subtilisin gene, for example, is a suitable sequence, as is any other signal peptide encoding sequence capable of directing the secretion of proteins in *B. subtilis*. The heterologous gene may be directly linked to the signal peptide encoding sequence or linked to the signal-encoding DNA through a translational fusion, involving protein-encoding DNA other than the *B. coagulans* amylase sequence. One construction suitable for both of these alternatives would contain the *B. subtilis* subtilisin signal peptide encoding sequence inserted immediately downstream of the *B. coagulans* amylase gene regulatory elements and amino-terminal protein-coding fragment. The *B. licheniformis* amylase gene could be inserted directly downstream from the subtilisin signal encoding sequence or, alternatively, a *B. licheniformis* amylase - APIII translation fusion could then be inserted.

DEPOSIT pCR46 has been deposited with the American Type Culture Collection, in Rockville, Md. (accession number 67736), under the terms of the Budapest Treaty. Applicants' assignee, BioTechnica International, Inc. acknowledges its responsibility to replace these cultures should they die before the end of the term of a patent issued hereon, and its responsibility to notify the ATCC of the issuance of such a patent, at which time the deposits will be made irrevocably available to the public for at least 30 years after the date of deposit or five years after the last request or the enforceable life of the patent, whichever is longer. Until that time the deposits will be made available to the Commissioner of Patents and all restraints upon availability should be irrevocably removed upon issuance of the patent under the terms of 37 CFR §1.14 and 35 USC §112..

OTHER EMBODIMENTS

Other embodiments are within the following claims. We claim:

1. A purified DNA sequence comprising the regulatory DNA naturally operationally associated with and positioned upstream from the *Bacillus coagulans* amylase gene represented by the nucleotide sequence depicted in FIG. 6, said purified DNA comprising less than the entire *Bacillus coagulans* chromosome.

2. A purified DNA sequence comprising the *Bacillus coagulans* amylase gene represented by the nucleotide sequence depicted in FIG. 6.

3. A vector comprising the regulatory DNA naturally operationally associated with and positioned upstream of the *Bacillus coagulans* amylase gene represented by the nucleotide sequence depicted in FIG. 6.

4. The vector of claim 1 further comprising, downstream of and in reading frame with said regulatory DNA, said *Bacillus coagulans* gene or a region thereof encoding at least the first two N-terminal amino acids of said *B. coagulans* amylase.

5. The vector of claim 2, wherein said region encodes at least the first 30 N-terminal amino acids of said *B. coagulans* amylase.

6. The vector of claim 1 or claim 2, further comprising, downstream of and in reading frame with said regulatory region, a site for insertion of a heterologous DNA sequence.

7. The vector of claim 6, wherein said heterologous DNA sequence is inserted at said site, expression of said heterologous DNA sequence being under the control of said regulatory region.

8. The vector of claim 7, said site for insertion of a heterologous DNA sequence being located within said *B. coagulans* amylase gene, so that said vector encodes a fusion polypeptide comprising a fragment of *B. coagulans* amylase fused to the polypeptide encoded by said heterologous DNA sequence.

9. The vector of claim 7, said site being located at the 3' end of said *B. coagulans* amylase gene, so that said vector encodes a fusion polypeptide comprising said *B. coagulans* amylase fused to the polypeptide encoded by said heterologous DNA sequence.

10. The vector of claim 7 further comprising a signal peptide encoding sequence capable of functioning in a gram positive cell and positioned upstream of and in reading frame with said heterologous DNA, to effect secretion of the polypeptide encoded by said heterologous DNA sequence from a host Bacillus cell transformed with said vector.

11. The vector of claim 10 wherein said signal peptide encoding sequence is a synthetic or cloned copy of signal peptide encoding DNA naturally associated with the genus Bacillus.

12. The vector of claim 11 wherein said signal peptide encoding sequence is a synthetic or cloned copy of signal peptide encoding DNA naturally associated with *Bacillus subtilis*.

13. The vector of claim 10 wherein said signal peptide encoding sequence is a sequence naturally associated with a Bacillus subtilisin gene.

14. The vector of claim 13 wherein said subtilisin gene encodes *Bacillus subtilis* subtilisin.

15. The vector of claim 11 wherein said signal peptide encoding sequence is a sequence naturally associated with a penicillinase gene from one of the following Bacillus species:
(a) *B. cereus*, or
(b) *B. licheniformis*.

16. The vector of claim 11 wherein said signal peptide encoding sequence is a sequence naturally associated with an alpha-amylase gene from one of the following Bacillus species:
(a) *B. subtilis*, or
(b) *B. licheniformis*.

17. The vector of claim 7 wherein said heterologous DNA encodes a medically useful protein.

18. The vector of claim 17 wherein said heterologous DNA encodes a hormone, an antitumor protein, an antiviral protein, an antibody or a clotting protein.

19. The vector of claim 17 wherein said heterologous DNA sequence encodes a growth factor.

20. The vector of claim 7 wherein said heterologous DNA sequence encodes atrial natriuretic factor or a biologically active fragment thereof.

21. The vector of claim 7 wherein said heterologous DNA encodes an agriculturally useful protein.

22. The vector of claim 7 wherein said heterologous DNA encodes an industrially useful protein.

23. A vector comprising a DNA sequence encoding *Bacillus coagulans* amylase as represented by the amino acid sequence depicted in FIG. 6.

24. A gram positive cell transformed with the vector of claim 1 or claim 5.

25. The cell of claim 24, said cell being a Bacillus cell.

26. The cell of claim 25 said cell being a *Bacillus subtilis* cell.

27. The cell of claim 25, said cell being one of the following Bacillus species:
(a) *B. licheniformis*,
(b) *B. amyloliquefaciens*,
(c) *B. polymyxa*,
(d) *B. stearothermophilus*,
(e) *B. thermoproteolyticus*,
(f) *B. coagulans*,
(g) *B. thuringiensis*,
(h) *B. megaterium*,
(i) *B. cereus*,
(j) *B. natto*, or
(k) *B. acidocaldarius*.

28. A method for producing *B. coagulans* amylase in a gram positive cell, said method comprising
providing a vector, said vector containing a DNA sequence encoding *B. coagulans* amylase as represented by the amino acid sequence depicted in FIG. 6,
transforming said cell with said vector,
culturing said transformed cell in culture medium to produce said amylase, and
isolating said amylase from said cultured cell or said medium.

29. A method for producing a heterologous polypeptide in a gram positive cell, said method comprising
providing the vector of claim 7,
transforming said cell with said vector,
culturing said transformed cell in culture medium to produce said heterologous polypeptide, and
isolating said protein from said cultured cell or said medium.

30. The method of claim 29 wherein the DNA encoding said heterologous polypeptide includes a signal peptide encoding sequence capable of functioning in a gram positive cell and effecting secretion of said heterologous protein from said cell.

31. The method of claim 30 wherein said signal peptide encoding sequence is a synthetic or cloned copy of signal peptide encoding DNA naturally associated with Bacillus.

32. The method of claim 31 wherein said signal peptide encoding sequence is a synthetic or cloned copy of signal peptide encoding DNA naturally associated with *Bacillus subtilis*.

33. The method of claim 31 wherein said Bacillus signal peptide encoding sequence encodes the signal peptide of a subtilisin gene.

34. The method of claim 31 wherein said subtilisin gene encodes *Bacillus subtilis* subtilisin.

35. The method of claim 30 wherein said signal peptide encoding sequence is a sequence naturally associated with a penicillinase gene from one of the following Bacillus strains:
(a) *B. cereus*, or
(b) *B. licheniformis*.

36. The method of claim 30 wherein said signal peptide encoding sequence is a sequence naturally associated with an alpha-amylase gene from one of the following Bacillus strains:
(a) *B. subtilis*, or
(b) *B. licheniformis*.

37. The method of claim 29 wherein said heterologous DNA encodes a medically useful protein.

38. The method of claim 37 wherein said heterologous DNA encodes a hormone, an antitumor protein, an antiviral protein, an antibody or a clotting protein.

39. The method of claim 37 wherein said heterologous DNA encodes a growth factor.

40. The method of claim 7 wherein said heterologous DNA encodes atrial natriuretic factor or a biologically active fragment thereof.

41. The method of claim 29 wherein said heterologous DNA encodes an agriculturally useful protein.

42. The method of claim 29 wherein said heterologous DNA encodes an industrially useful protein.

* * * * *

UNITED STATES PATENT AND TRADEMARK OFFICE
CERTIFICATE OF CORRECTION

PATENT NO. : 5,171,673
DATED : December 15, 1992
INVENTOR(S) : Alan Sloma et al

It is certified that error appears in the above-indentified patent and that said Letters Patent is hereby corrected as shown below:

Column 4, line 20, after "that the", insert the following:
"B. coagulans pNH237 clone directed the production of".

Column 5, line 37, correct he spelling of "oligonucleotide".

Signed and Sealed this

Eleventh Day of January, 1994

Attest:

BRUCE LEHMAN

Attesting Officer  Commissioner of Patents and Trademarks